US012766258B2

(12) United States Patent
Bartee et al.

(10) Patent No.: US 12,766,258 B2
(45) Date of Patent: Oct. 20, 2026

(54) TDD TRACKING APPROACHES FOR INSULIN DELIVERY SYSTEMS, METHODS, AND DEVICES

(71) Applicant: myLife Diabetes Care AG, Burgdorf (CH)

(72) Inventors: Amy Kathleen Bartee, Westfield, IN (US); Ahmad Mohamad Haidar, Montreal (CA); Richard Earl Jones, Jr., Monrovia, IN (US)

(73) Assignee: myLife Diabetes Care AG, Burgdorf (CH)

(*) Notice: Subject to any disclaimer, the term of this patent is extended or adjusted under 35 U.S.C. 154(b) by 816 days.

(21) Appl. No.: 17/998,215

(22) PCT Filed: May 7, 2021

(86) PCT No.: PCT/US2021/031216
§ 371 (c)(1),
(2) Date: Nov. 8, 2022

(87) PCT Pub. No.: WO2021/236351
PCT Pub. Date: Nov. 25, 2021

(65) Prior Publication Data
US 2023/0218821 A1 Jul. 13, 2023

Related U.S. Application Data

(60) Provisional application No. 63/028,964, filed on May 22, 2020.

(51) Int. Cl.

| | |
|---|---|
| ***A61M 5/172*** | (2006.01) |
| ***A61M 5/168*** | (2006.01) |
| ***G16H 20/17*** | (2018.01) |

(52) U.S. Cl.
CPC ...... *A61M 5/1723* (2013.01); *A61M 5/16877* (2013.01); *G16H 20/17* (2018.01); *A61M 2202/0486* (2013.01)

(58) Field of Classification Search
CPC ............ A61M 5/1723; A61M 5/16877; A61M 2202/0486; G16H 20/17; G16H 40/63; G16H 50/20
See application file for complete search history.

(56) References Cited

U.S. PATENT DOCUMENTS

2003/0130616 A1* 7/2003 Steil .................... A61B 5/1495 600/365
2009/0156924 A1 6/2009 Shariati et al.
(Continued)

FOREIGN PATENT DOCUMENTS

WO 2009/133558 11/2009
WO 2017/124006 7/2017
(Continued)

OTHER PUBLICATIONS

International Search Report of the International Searching Authority pertaining to International Application No. PCT/US2021/031216; Date of Mailing: Sep. 20, 2021; 7 pages.
(Continued)

*Primary Examiner* — Wesley G Harris
*Assistant Examiner* — Neeraja Gollamudi
(74) *Attorney, Agent, or Firm* — Dorsey & Whitney LLP

(57) ABSTRACT

A system includes a controller that is in communication with a medication delivery device and that includes control logic. The control logic is operative to calculate a first filtered total daily dose (TDD) during an initial tracking phase based, at least in part, on a first set of insulin delivery doses and subject to a first set of rate limits. The control logic is also operative to calculate a second filtered TDD during a steady
(Continued)

state tracking phase based, at least in part, on a second set of insulin delivery doses and subject to a second set of rate limits.

20 Claims, 4 Drawing Sheets

(56) References Cited

U.S. PATENT DOCUMENTS

| | | | | |
|---|---|---|---|---|
| 2014/0066887 | A1* | 3/2014 | Mastrototaro | A61B 5/4839 604/506 |
| 2014/0276574 | A1 | 9/2014 | Saint | |
| 2014/0303552 | A1 | 10/2014 | Kanderian et al. | |
| 2016/0256629 | A1* | 9/2016 | Grosman | A61B 5/14532 |

FOREIGN PATENT DOCUMENTS

| | | | | |
|---|---|---|---|---|
| WO | WO-2018204568 A1 * | 11/2018 | | G16H 20/17 |
| WO | 2019/246381 | 12/2019 | | |

OTHER PUBLICATIONS

Written Opinion of the International Searching Authority pertaining to International Application No. PCT/US2021/031216; Date of Mailing: Sep. 20, 2021; 10 pages.
First Examination Report issued in Australian Patent Application No. 2024278548, mailed on Feb. 24, 2026, 4 pages.
Lunze, et al., "Blood Glucose control Algorithms for Type 1 Diabetic Patients: A methodological Review", Biomedical Signal Processing and Control, vol. 8, No. 2, pp. 107-119, Mar. 2013.

* cited by examiner

TDD TRACKING APPROACHES FOR INSULIN DELIVERY SYSTEMS, METHODS, AND DEVICES

FIELD OF THE DISCLOSURE

The present disclosure relates to the control of physiological glucose concentrations. More particularly, the present disclosure relates to closed loop systems and methods for controlling physiological glucose concentrations in a patient.

BACKGROUND

Subcutaneous insulin replacement therapy has proven to be the regimen of choice to control diabetes. Insulin is administered via either multiple daily injections or an infusion pump with dosages being informed by capillary glucose measurements made several times a day by a blood glucose meter. This conventional approach is known to be imperfect as day to day (and in fact moment to moment) variability can be significant. Further, this approach can be burdensome to the patient as it requires repeated finger sticks, a rigorous monitoring of food intake, and vigilant control of insulin delivery.

The advent of glucose measurement devices such as a continuous glucose monitor (CGM) creates the potential to develop a closed loop artificial pancreas (AP) system. An AP system uses glucose data provided by the CGM in a dosing/control algorithm executed on a controller that provides direction to an infusion pump, and the pump administers medication to the patient.

SUMMARY

In Example 1, a system to control glucose in a patient is disclosed. The system includes a controller configured to communicate with a medication delivery device. The controller includes control logic operative to calculate a first filtered total daily dose (TDD) during an initial tracking phase based, at least in part, on a first set of insulin delivery doses and subject to a first set of rate limits. The control logic is further operative to calculate a second filtered TDD during a steady state tracking phase based, at least in part, on a second set of insulin delivery doses and subject to a second set of rate limits.

In Example 2, the system of Example 1, wherein the control logic is further operative to set a first system gain based, at least in part, on the first filtered TDD and set of second system gain based, at least in part on the second filtered TDD.

In Example 3, the system of Example 2, wherein the control logic is further operative to calculate a first set of basal doses based, at least in part, on the first system gain and calculate a second set of basal doses based, at least in part on the second system gain.

In Example 4, the system of any of the preceding Examples, wherein the first set of rate limits includes a first upper limit and a first lower limit, wherein the second set of rate limits includes a second upper limit and a second lower limit, and wherein the first set of rate limits permit greater TDD rate changes than the second set of rate limits.

In Example 5, the system of Example 4, wherein the second lower limit permits a greater absolute rate change than the second upper limit.

In Example 6, the system of any of the preceding Examples, wherein the first set of insulin delivery doses are based on fewer TDD measurements than the second set of insulin delivery doses.

In Example 7, the system of any of the preceding Examples, wherein the control logic is operative to transition to the steady state tracking phase after applying the initiation tracking phase for a period of time or in response to a pre-determined number of valid actual TDD measurements.

In Example 8, the system of any of the preceding Examples, wherein the control logic is further operative to calculate an estimated TDD at start-up of an initialization phase based, at least in part, on a total daily basal (TDB) level.

In Example 9, the system of Example 8, wherein the estimated TDD is a pre-determined ratio of TDB.

In Example 10, the system of any of the preceding Examples, wherein the first filtered TDD and the second filtered TDD are limited to a pre-determined ratio of total daily basal.

In Example 11, the system of any of the preceding Examples, wherein the control logic is operative to calculate the first filtered TDD during the initial tracking phase once per day and calculate the second filtered TDD during the steady state tracking phase once per day.

In Example 12, the system of any of the preceding Examples, wherein the control logic is operative to calculate the first filtered TDD by processing the first set of insulin delivery doses with an infinite impulse response (IIR) filter and calculate the second filtered TDD by processing the second set of insulin delivery doses with the IIR filter.

In Example 13, the system of any of the preceding Examples, further including the medication delivery device configured to deliver insulin to the patient based, at least in part, to the first filtered TDD during the initiation tracking phase and the second filtered TDD during the steady state tracking phase.

In Example 14, the system of any of the preceding Examples, further including a glucose measurement device in communication with the controller and configured to measure the glucose level.

In Example 15, a method is disclosed. The method includes calculating, by a controller applying a digital filter, a first filtered total daily dose (TDD) during an initial tracking phase based, at least in part, on a first set of insulin delivery doses and subject to a first set of rate limits. The method further includes calculating, by the controller, a first set of basal rates based, at least in part, on the first filtered TDD. The method further includes calculating, by the controller applying the digital filter, a second filtered TDD during a steady state tracking phase based, at least in part, on a second set of insulin delivery doses and subject to a second set of rate limits. The method further includes calculating, by the controller, a second set of basal rates based, at least in part, on the second filtered TDD.

In Example 16, the method of Example 15, further including delivering, by a medication delivery device, amounts of insulin responsive to the first set of basal rates. The method also includes delivering, by the medication delivery device, amounts of insulin responsive to the second set of basal rates.

In Example 17, the method of Examples 15 and 16, further including setting a first system gain based, at least in part, on the first filtered TDD and setting of second system gain based, at least in part on the second filtered TDD. The first set of basal rates are based, at least in part, on the first system gain. The second set of basal rates are based, at least in part, on the second system gain.

In Example 18, the method of any of Examples 15-17, further including calculating an estimated TDD during an initialization phase based, at least in part, on a total daily basal level.

In Example 19, the method of any of Examples 15-18, wherein the first filtered TDD and the second filtered TDD are limited to a pre-determined ratio of a total daily basal level.

In Example 20, a non-transitory computer-readable medium is disclosed. The non-transitory computer-readable medium includes instructions that, when executed, cause a hardware processor to calculate a first filtered total daily dose (TDD) during an initial tracking phase based, at least in part, on a first set of insulin delivery doses and subject to a first set of rate limits and calculate a second filtered TDD during a steady state tracking phase based, at least in part, on a second set of insulin delivery doses and subject to a second set of rate limits.

In Example 21, a non-transitory computer-readable medium is disclosed. The non-transitory computer-readable medium includes instructions that, when executed, cause a hardware processor to carry out the steps of the method of Examples 15-19.

Figure 1:
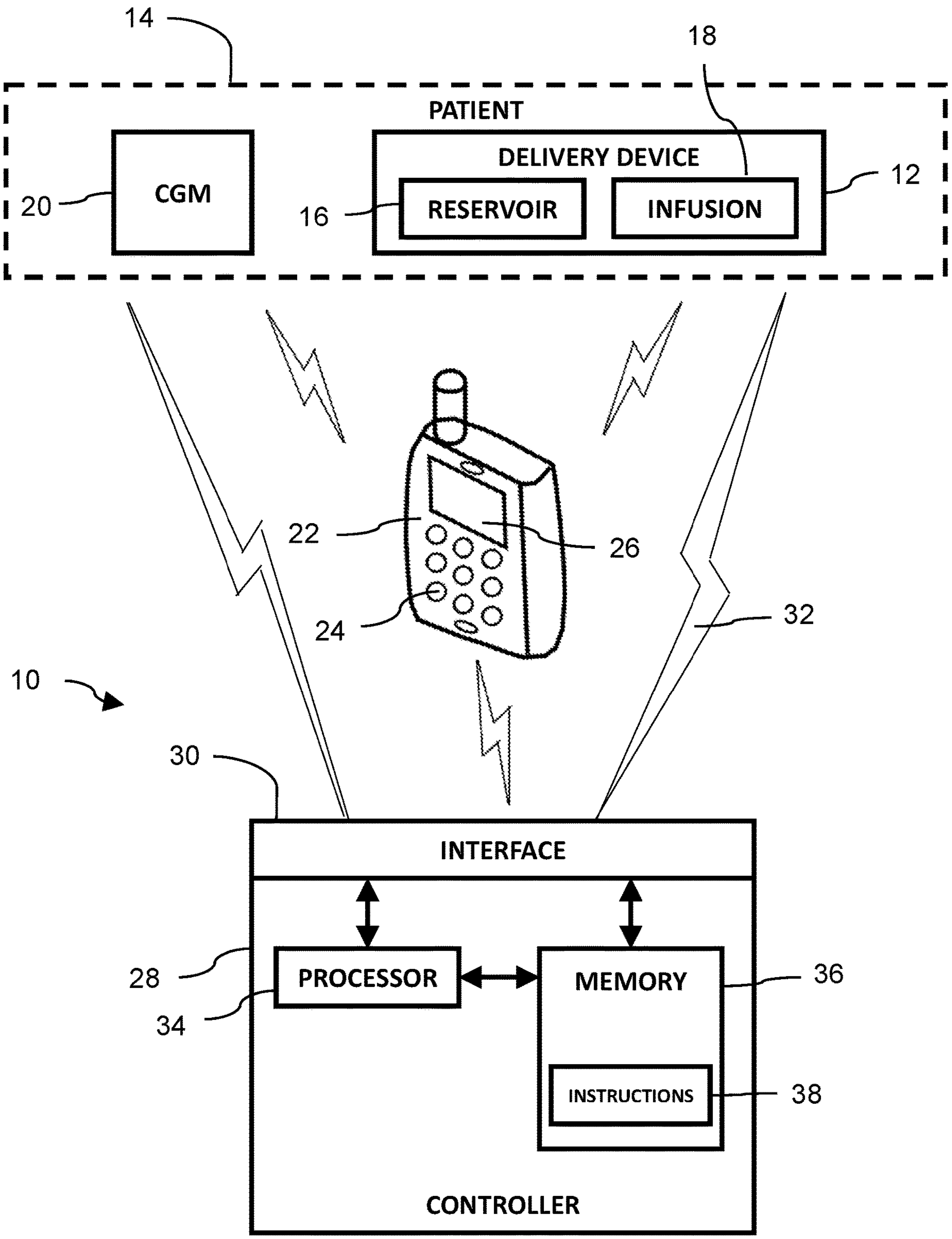
FIG. 1 shows a schematic of a system for controlling physiological glucose, in accordance with certain embodiments of the present disclosure.

While the disclosure is amenable to various modifications and alternative forms, specific embodiments have been shown by way of example in the drawings and are described in detail below. The intention, however, is not to limit the disclosure to the particular embodiments described but instead is intended to cover all modifications, equivalents, and alternatives falling within the scope the appended claims.

DETAILED DESCRIPTION

Closed loop insulin delivery systems automatically adjust insulin delivery in response to measured glucose levels. As will be described in more detail below, these systems automatically adjust a basal insulin delivery rate at regular intervals, such as every 5 to 15 minutes, based, at least in part, on information such as a patient's estimated insulin sensitivity.

Insulin sensitivity is a component that estimates how a patient reacts to insulin deliveries and that is used in various calculations in closed loop insulin delivery systems. A high insulin sensitivity indicates that the patient's glucose levels will change more for a given insulin dose amount compared to a patient with a lower insulin sensitivity.

A patient's total daily dose (TDD) of insulin can be used as an indirect measure or proxy for the patient's insulin sensitivity. However, a patient's TDD will vary over time due to both physiological and behavior changes. Certain embodiments of the present disclosure are accordingly directed to systems, methods, and devices for filtering TDD.

System Hardware

FIG. 1 depicts an exemplary representational block diagram of a system 10 for controlling physiological glucose. The system 10 includes a medication delivery device 12 such as an infusion pump which is removably coupled to a patient 14. The medication delivery device 12 includes at least one medication reservoir 16 which contains a medication. In the illustrated embodiment, the medication or drug includes an insulin, such as a regular insulin, an insulin analog such as insulin lispro and insulin glargine, and an insulin derivative, for example. The medication delivery device 12 may deliver at least one medication (e.g., insulin) to a patient 14 via an infusion set 18, which providing a fluid path from the medication delivery device 12 to the patient 14. The infusion set 18 may, for example, provide a fluid path from the medication delivery device 12 to a subcutaneous destination within the patient 14. The medication delivery device 12 or infusion set 18 may include a needle or cannula for inserting into the subcutaneous tissue of the patient. The medication reservoir 16 can be coupled to a separate pumping device (e.g., plunger, actuator, motor) that assists with pumping medication from the reservoir to the patient.

The system 10 also includes an analyte sensor such as a glucose measurement device 20. The glucose measurement device 20 may be a standalone device or may be an ambulatory device. One example of a glucose measurement device is a continuous glucose monitor (CGM). In specific embodiments, the glucose measurement device 20 may be a glucose sensor such as a Dexcom G6 series continuous glucose monitor, although any suitable continuous glucose monitor may be used. The glucose measurement device 20 is illustratively worn by the patient 14 and includes one or more sensors in communication with or monitoring a physiological space (e.g., an interstitial or subcutaneous space) within the patient 14 and able to sense an analyte (e.g., glucose) concentration of the patient 14. In some embodiments, the glucose measurement device 20 reports a value that is associated with the concentration of glucose in the interstitial fluid, e.g., interstitial glucose (IG). The glucose measurement device 20 may transmit a signal representative of an IG value to the various other components of the system 10.

The system 10 includes a user interface device 22 (hereinafter the "UI 22") that may be used to input user data to the system 10, modify values, and receive information, prompts, data, etc., generated by the system 10. In certain embodiments, the UI 22 is handheld user device programmed specifically for the system 10 or may be implemented via an application or app running on the medication delivery device 12 or a personal smart device such as a phone, tablet, watch, etc. The UI 22 may include input devices 24 (e.g., buttons, switches, icons) and a display 26 that displays a graphical user interface (GUI). The user can interact with the input devices 24 and the display 26 to provide information (e.g., alphanumeric data) to the system 10. In certain embodiments, the input devices 24 are icons (e.g., dynamic icons) on the display 26 (e.g., touchscreen). In one example, a patient uses the UI 22 to announce events such as a meal, start of exercise, end of exercise, emergency stop, etc. In some embodiments, the UI 22 is a graphical user interface (GUI) with a display, where the user interacts with presented information, menus, buttons, etc., to receive information from and provide information to the system 10.

The system 10 also includes a controller 28. Although the controller 28 is shown as being separate from the medication delivery device 12 and the UI 22, the controller 28 can be physically incorporated into either the medication delivery device 12 or the UI 22 or carried out by a remote server. Alternatively, the UI 22 and the medication delivery device 12 may each include a controller 28 and control of the system 10 may be divided between the two controllers 28. Regardless of its physical location within the system 10, the controller 28 is shown as being directly or indirectly communicatively coupled to the medication delivery device 12, the glucose measurement device 20, and the UI 22.

The controller 28 can include or be communicatively coupled to one or more interfaces 30 to communicatively couple via one or more communication links 32 to the medication delivery device 12, the glucose measurement device 20, and/or the UI 22. Example interfaces 30 include wired and wireless signal transmitters and receivers. Example communication links 32 include a wired communication link (e.g., a serial communication), a wireless communication link such as, for example, a short-range radio link, such as Bluetooth, IEEE 802.11, a proprietary wireless protocol, and/or the like. The term “communication link” may refer to an ability to communicate some type of information in at least one direction between at least two devices. The communication links 32 may be a persistent communication link, an intermittent communication link, an ad-hoc communication link, and/or the like. Information (e.g., pump data, glucose data, drug delivery data, user data) may be transmitted via the communication links 32. The medication delivery device 12, the glucose measurement device 20, and/or the UI 22 may also include one or more interfaces to communicatively couple via one or more communication links 32 to the other devices in the system 10.

The controller 28 can include at least one processor 34 (e.g., a microprocessor) that executes software and/or firmware stored in memory 36 of the controller 28 and that is communicatively coupled to the one or more interfaces 30 and to each other. The software/firmware code contains instructions that, when executed by the processor, cause the controller 28 to perform the functions of the control algorithm described herein. The controller 28 may alternatively or additionally include one or more application-specific integrated circuits (ASICs), field-programmable gate arrays (FPGAs), digital signal processors (DSPs), hardwired logic, or combinations thereof. The memory 36 may include computer-readable storage media in the form of volatile and/or nonvolatile memory and may be removable, non-removable, or a combination thereof. In embodiments, the memory 36 stores executable instructions 38 (e.g., computer code, machine-useable instructions, and the like) for causing the processor 34 to implement aspects of embodiments of system components discussed herein and/or to perform aspects of embodiments of methods and procedures discussed herein, including the control logic described in more detail below. The interfaces 30, the processor 34, and the memory 36 may be communicatively coupled by one or more busses. The memory 36 of the controller 28 is any suitable computer readable medium that is accessible by the processor. Memory may be a single storage device or multiple storage devices, may be located internally or externally to the controller 28, and may include both volatile and non-volatile media. Exemplary memory includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the controller 28.

The controller 28 may receive information from a plurality of components of the system 10 and feed the information (e.g., pump data, glucose data, drug delivery data, user data) into a control algorithm (as described in more detail below) which determines at least one drug delivery control parameter which may in part govern operation of the medication delivery device 12. In some specific embodiments, the controller 28 may receive pump data from the medication delivery device 12, glucose data from the glucose measurement device 20, and user data from the UI 22. The pump data received may include drug delivery data corresponding to drug dosages delivered to the patient 14 by the medication delivery device 12. The pump data may be supplied by the medication delivery device 12 as doses are delivered or on a predetermined schedule. The glucose data received by the controller 28 may include glucose concentration data from the glucose measurement device 20. The glucose data may be supplied at a continuous rate, occasionally or at predefined intervals (e.g., every 5 or 10 minutes).

The pump data, glucose data, drug delivery data, and user data may be provided to the controller 28 as acquired, on a predefined schedule or queued in the memory 36 and supplied to the controller 28 when requested. The user data may be input to the UI 22 in response to user/patient prompts generated by the UI 22 and/or declared by the patient 14 as instructed during training. In some embodiments, at least some of the pump data, glucose data, and/or user data may be retrieved from the memory 36 associated with the controller 28, and some of this data may be retrieved from a memory in the medication delivery device 12. In some embodiments, user interaction with the UI 22 may be minimal with the patient 14 being prompted to start execution of the algorithm implemented by the controller 28 and provide meal and/or exercise announcements. In other embodiments, the user may be prompted to provide various additional data in order to initialize the algorithm implemented by the controller 28.

The at least one drug delivery parameter determined by the controller 28 may be a medication dose or doses, which may at least in part govern drug administration to the patient 14 via the medication delivery device 12. For insulin delivery (e.g., delivery of a rapid acting insulin or ultra-rapid acting insulin), the drug delivery parameter may be a basal rate (e.g., a basal profile including predefined time-varying insulin flow rates over the course of 24 hours), micro-bolus doses (e.g., corrected doses with respect to the basal rate), and/or a meal bolus. The basal delivery is the continuous delivery of insulin at the basal rate needed by the patient to maintain the glucose level in the patient's blood at the desired level outside of post-meal periods. The medication delivery device 12 may provide the basal delivery in basal doses followed by periods of zero flow that average out to the basal rate. In one example, the medication delivery device 12 supplies a basal dose at a fixed interval, and the basal dose is equal to the desired basal rate times the duration of the interval. Occasionally, the user may require a larger amount of insulin due to a change in activity such as eating a meal or other activities that affect the user's metabolism. This larger amount of insulin is herein referred to as a bolus. A meal bolus is a specific amount of insulin that is generally supplied over a short period of time. The nature of the medication delivery device 12 may require delivering the bolus as a continuous flow of insulin for a period or as a series of smaller, discrete insulin volumes supplied over a period. The meal bolus facilitates maintenance of the glucose level as the digestive system supplies a large amount of glucose to the blood stream.

In one embodiment, the drug delivery parameter provided to the medication delivery device 12 is a control signal requesting the pump to deliver a specific amount or volume of medication. In one embodiment, the drug delivery parameter is an analog or digital signal that the medication delivery device 12 converts to an amount or volume of medication or a number of pump strokes. In some embodiments, the drug delivery parameter is a deviation from the basal insulin dose or current value of the basal insulin profile. The deviation may be an amount or volume of insulin or a percentage of the basal insulin dose. Thus, the system 10 may operate in a closed-loop setting requiring minimal or no interaction from the patient 14 after initial start-up to effect glycemic control.

The term physiological glucose herein refers to the measured concentration of glucose in the body. In some embodiments, physiological glucose may be the concentration of glucose in the blood, which may also be referred to as blood glucose. In other embodiments, physiological glucose may be the concentration of the glucose in the blood plasma, which may be referred to as plasma glucose. The measured value of plasma glucose is typically 10 to 12% higher than blood glucose because the blood cells of the blood have been removed in the plasma glucose determination. The relationship between plasma glucose and blood glucose depends on the hematocrit and can vary from patient to patient and over time. The physiological glucose, abbreviated herein as PG, may be measured indirectly by measuring the glucose concentration in the interstitial fluid which is referred to as interstitial glucose and abbreviated IG.

MMPC Algorithm

Figure 2:
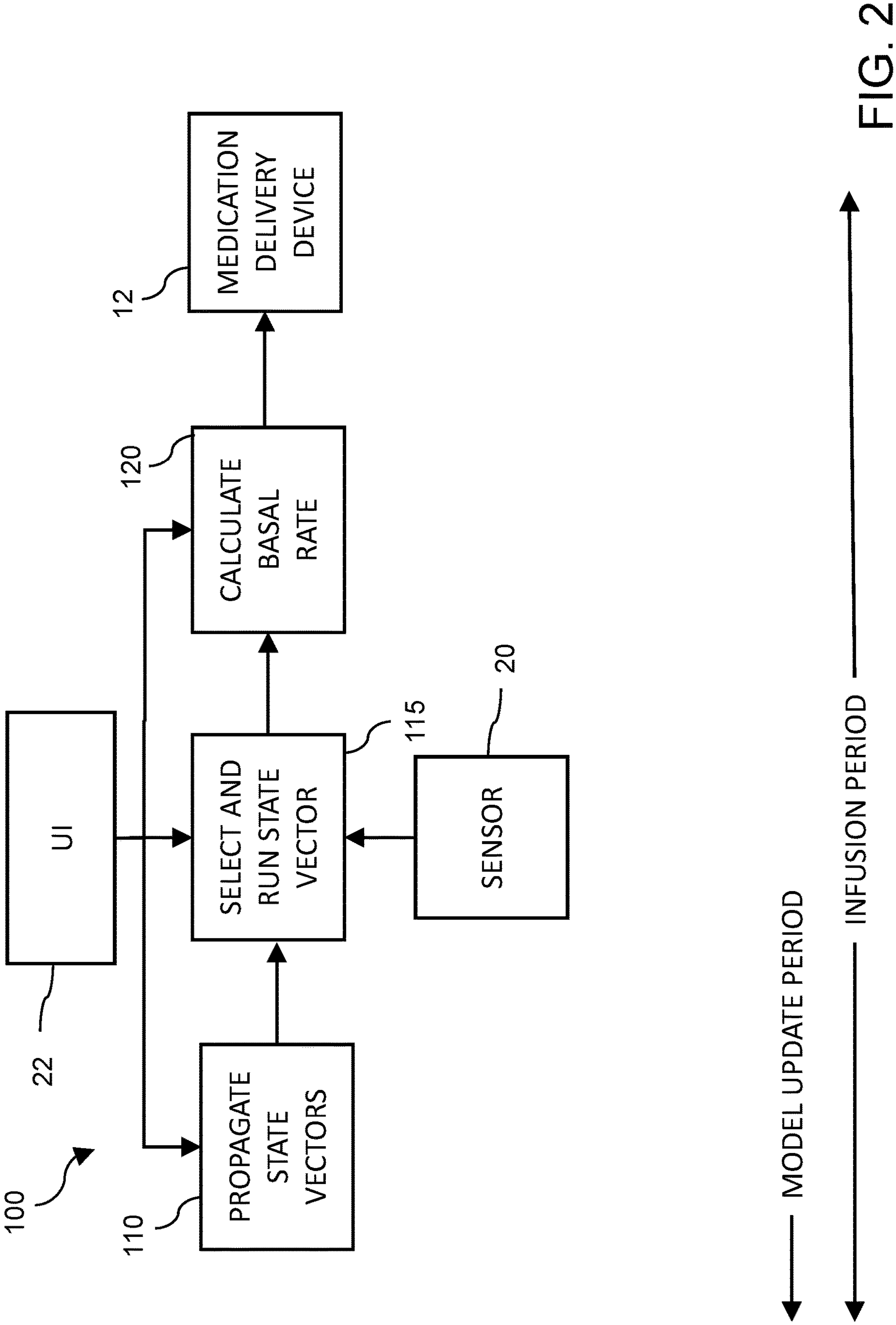
FIG. 2 shows a block diagram of an exemplary model predictive control algorithm, in accordance with certain embodiments of the present disclosure.

In certain embodiments, the controller 28 has control logic in the form of a multi-model predictive controller (MMPC) 100, which is outlined in FIG. 2 and which executes an artificial pancreas algorithm. In other embodiments, the controller 28 has control logic in the form of a proportional-integral-derivative (PID) controller or other types of closed-loop control approaches. Although the description below uses the MMPC 100, other approaches such as PID controllers can be used in connection with the claimed invention.

The MMPC 100 receives glucose concentration data from the glucose measurement device 20 and user data from the UI 22 and determines the amount of medication for the medication delivery device 12 to deliver to the patient 14. The medication delivery device 12 then delivers the requested insulin dose to the patient via the infusion set 18.

The MMPC 100 combines multiple state vectors and their models with a model predictive control algorithm. The MMPC 100 adds improved adaptability to changes in the body and the environment to the controller 28 by propagating multiple state vectors (block 110 in FIG. 2) and selecting the state vector and its model that best matches past data. The selected-state vector and its model are then used by the controller 28 to determine the next basal rate or basal dose of insulin to deliver to the patient in order to achieve the desired physiological glucose level (block 115 in FIG. 2). The use of the multiple state vectors and their models improves the responsiveness of the algorithm to changes in metabolism, digestion, activity or other changes.

In certain embodiments, the MMPC 100 propagates each of the state vectors at each time interval using models, glucose data and covariance matrices with a Kalman filter. In some embodiments, the MMPC 100 retains the previous values of each state vector for a period of time and as each state vector is propagated generating the most current value of each state vector, the oldest value of each state vector is overwritten. Each state vector is associated with a unique model and unique covariance matrices. The MMPC 100 selects a best state vector and its model based on how well the state variable for IG matches the measured values of IG over a period in the past. The MMPC 100 then uses in the selected-state vector and its model in a model-predictive controller where the MMPC 100 propagates the selected-state vector out to a prediction horizon generating a predicted set of physiological glucose values over time. The set of predicted glucose values at corresponding time is herein referred to as a predicted trajectory. The MMPC 100 uses the physiological glucose trajectory and an objective function to determine an optimal insulin trajectory.

In some embodiments, the optimal insulin trajectory is a trajectory of deviations from the basal insulin or basal profile, herein referred to as the basal-deviation trajectory. In these embodiments, the amount of insulin delivered to the body is the predefined basal insulin plus the optimal-basal deviation determined from the insulin trajectory. In these embodiments, the model and the objective function consider the response of the body to meals and insulin levels above or below the predefined basal insulin rate.

A preliminary insulin rate, dose or optimal-basal deviation is taken from the value of the insulin trajectory for the first interval. The MMPC 100 may limit this preliminary insulin rate, dose or optimal-basal deviation before passing the rate or dose request to the medication delivery device 12. In the embodiments where the optimal insulin trajectory is the deviation from the basal profile, the dose request is the sum of the limited-basal deviation plus basal profile. The limited insulin rate, limited dose, or limited-basal deviation is then fed back into the multiple state vectors as an insulin input for the determination of the insulin rate or dose at the next interval.

Target Glucose

As described above, the illustrative MMPC algorithm 100 implemented by the controller 28 uses a target physiological glucose value ($PG_{TGT}$) when determining the optimal deviation from the basal profile. The $PG_{TGT}$ is a fixed value in some embodiments. In other embodiments, $PG_{TGT}$ is modified from a nominal or preset value when various conditions are present or various events occur. The target physiological glucose value may be determined based on user data communicated to the system 10 via the UI's inputs. Such adjustments of the target physiological glucose value may, for example, occur in response to the announcement of meals and/or exercise. The adjustments of the target glucose value may be governed at least in part by a target modification formula or may be based off predefined values to be used when the certain circumstances exist. Additionally, a target value adjustment may persist for a period after the condition or event occurs. The adjustment may be a static or fixed adjustment over this period or alter in magnitude (e.g., decrease linearly in magnitude) as the time period elapses.

The glucose target may be used to determine the optimal deviations from the basal profile as described above. The target physiological glucose value may be altered in response to meal and exercise input data. As part of determining the optimal deviation in the basal profile, the nominal target glucose value may be adjusted from its nominal value. An exemplary nominal target glucose value is 5-6 mmol/L, although other suitable values and ranges (e.g., 5-5.5 mmol/L) may be implemented. The target glucose value may be adjusted in some embodiments if the patient 14 has announced exercise and not yet ended exercise while the MMPC 100 is determining the optimal deviation of the basal profile. In other embodiments, the target glucose value may be modified for exercise if a period of exercise has occurred for a predetermined period within a predefined time of the current time. In some embodiments, meal data may alter the target physiological glucose value if the patient 14 has announced a meal within a predefined period of the determination of the optimal-basal deviation.

An exercise announcement may modify the physiological glucose target value from a preset or nominal value to an exercise target value. In some embodiments, the exercise target value may be at or about 3 mmol/L greater than the preset or nominal target value. In some embodiments, the preset or nominal target value may be at or about 6 mmol/L and the exercise target value may be at or about 9 mmol/L.

A meal announcement or meal data may be input to a formula which increases the target value based on proximity to the meal. The formula may be arranged such that the meal has a greater effect on the target values in close temporal proximity to the meal. As the time from the consumption of the meal increases, the target value may be altered to a lesser degree. After a certain predefined time period has elapsed, the meal input data may no longer have an effect in determining any target value adjustment and a preset or nominal target value may be used. The effect of the meal event on the target physiological glucose value may change (e.g., decrease) in a linear fashion over time.

After accounting for the above-described announcements, the MMPC 100 calculates a basal rate (block 120 in FIG. 2) and transmits that basal rate to the medication delivery device 12.

The Models

A model of the MMPC 100 includes a set of linear difference equations executed by control logic that calculate levels of PG and the IG in a patient's body. In some embodiments, the model comprises eight compartments that track the movement and the persistence of insulin, carbohydrates, and glucose within the body. In some embodiments, the model considers external sources of glucose (carbohydrates) and levels of insulin different from the basal profile.

The movement and persistence of insulin, carbohydrates, and glucose may be driven by several model parameters. The calculated PG values may be used to determine the next micro-bolus of insulin and/or a meal bolus that may be delivered to the patient. The calculated IG may be compared to the measured IG. The MMPC 100 may comprise a large set of state vectors that each have a model with a unique combination of model parameters.

The model parameters may include but are not limited to insulin sensitivity ($S_I$), insulin time constant ($k_I$), the meal action time constant ($k_C$), sensor time constant ($k_{SENSOR}$), insulin to carbohydrate ratio (ICR). The model parameters may also include input values at the UI 22, programmed values in the algorithm, or stored values in the memory 36 readable by the controller 28, or a combination of these options.

As noted above, insulin sensitivity is a component that estimates how a patient reacts to insulin deliveries. A high insulin sensitivity indicates that the patient's glucose levels will change more for a given insulin dose amount compared to a patient with a lower insulin sensitivity. Insulin sensitivity is typically expressed in terms of mg/dl per unit of insulin or mmol/l per unit.

User data may include but is not limited to insulin/carbohydrate ratio, meal size, carbohydrate ratio of meal, and exercise. User data may also include a group of data that herein is referred to as insulin need data. The insulin need data may include but is not limited to a basal dose, a basal profile, total daily insulin dose (TDD), and total daily basal insulin dose (TDB).

In certain embodiments, the basal dose is an open loop or nominal insulin dose needed by the user for a predefined period. In one example, the basal dose is the amount of insulin needed by the user for the duration of each period or interval between glucose measurements received by the controller from the CGM. In another example, the basal dose at time t is the basal profile at time t. In the illustrative embodiment, the basal profile is a predefined time-varying insulin flow rate over the course of 24 hours. In one example, the basal profile may be expressed as a list of insulin flow rates or a paired list of flow rates and times. In another example, the basal profile may be expressed as an equation.

TDD

As noted above, a patient's TDD can be used as an indirect measure or a proxy for the patient's insulin sensitivity. Put another way, an estimate of a patient's sensitivity can be derived from the patient's TDD. Insulin sensitivity may be used by the MMPC 100 as an input to set the overall gain (e.g., aggressiveness) of the MMPC 100 such that insulin doses are appropriately sized. For example, a lower gain level may be used for patients with high insulin sensitivity so that the MMPC 100 calculates smaller control insulin doses to control the patient's blood glucose. Further, as noted above, TDD itself may be used by the MMPC 100 to ultimately determine amounts of insulin to deliver to the patient.

In certain embodiments, the TDD is the sum of all the insulin delivered to the patient over a 24-hour period, and the TDB is the sum of all the basal insulin deliveries over the 24-hour period. In one embodiment, the TDB is approximately equal to the TDD minus the sum of meal boluses and correction mini-boluses. In certain embodiments, the TDD and TDB are calculated regularly (e.g., daily) by the controller 28.

However, a patient's TDD will vary over time due to both physiological and behavior changes. Long term effects include aging and diabetes progression, short term effects include seasonal changes (e.g., patients may be more active in warmer weather), and abrupt effects include illnesses and large meals. For example, a large meal bolus will contribute to a patient's TDD but the larger TDD is not indicative that the patient's insulin sensitivity has decreased. Also, TDD may reflect behaviors and lifestyle instead of pure insulin sensitivity. For example, different patients may have the same or similar sensitivity but one patient may, on average, eat lower-carb meals and therefore have a lower TDD.

As such, TDD can vary by the hour and the variations may be based on factors that are not indicative of a patient's insulin sensitivity. The description below describes approaches for calculating a filtered TDD that, at least partially, removes variations in TDD that are not indicative of changes in insulin sensitivity. The approach for calculating the filtered TDD may be different at different time periods.

Initialization Phase, Initial Tracking Phase, and Steady State Tracking Phase

When the system 10 is initially started during an initialization phase, TDD can be estimated by the controller 28 until the system 10 has delivered insulin over enough time to calculate actual TDD.

As one example, during the initialization phase, the estimated TDD can be calculated based, at least in part, on the TDB level—which could be the total basal calculated from a programmed basal profile. In addition, the estimated TDD can be calculated based, at least in part, on an insulin sensitivity factor, body weight, and/or ICR. As another example, the estimated TDD can be a pre-determined ratio of TDB. More specifically, the TDD estimate can be calculated as TDB/fraction with the fraction ranging from 0.5-0.8 (e.g., 0.5, 0.6, 0.7, 0.8).

Estimating TDD during the initialization phase—as opposed to basing the TDD off patients' manual entry of past doses—can be less prone to errors in the event a patient initially manually enters inaccurate dosage information. As such, the MMPC 100 (or another type of control approach such as a PID controller) can use the estimated TDD for its various calculations during the initialization phase.

Once the system 10 can calculate at least one day of actual TDD (e.g., three days of actual TDD), the system 10 can transition to an initial tracking phase and then later to a steady state tracking phase. During both phases, the controller 28 is configured to calculate a filtered TDD based, at least in part, on the actual TDD. If actual TDD is not available for a number of days (e.g., 3 or more days), the system 10 can transition back to the initialization phase for re-initialization once actual TDD calculations are available again.

Figure 3:
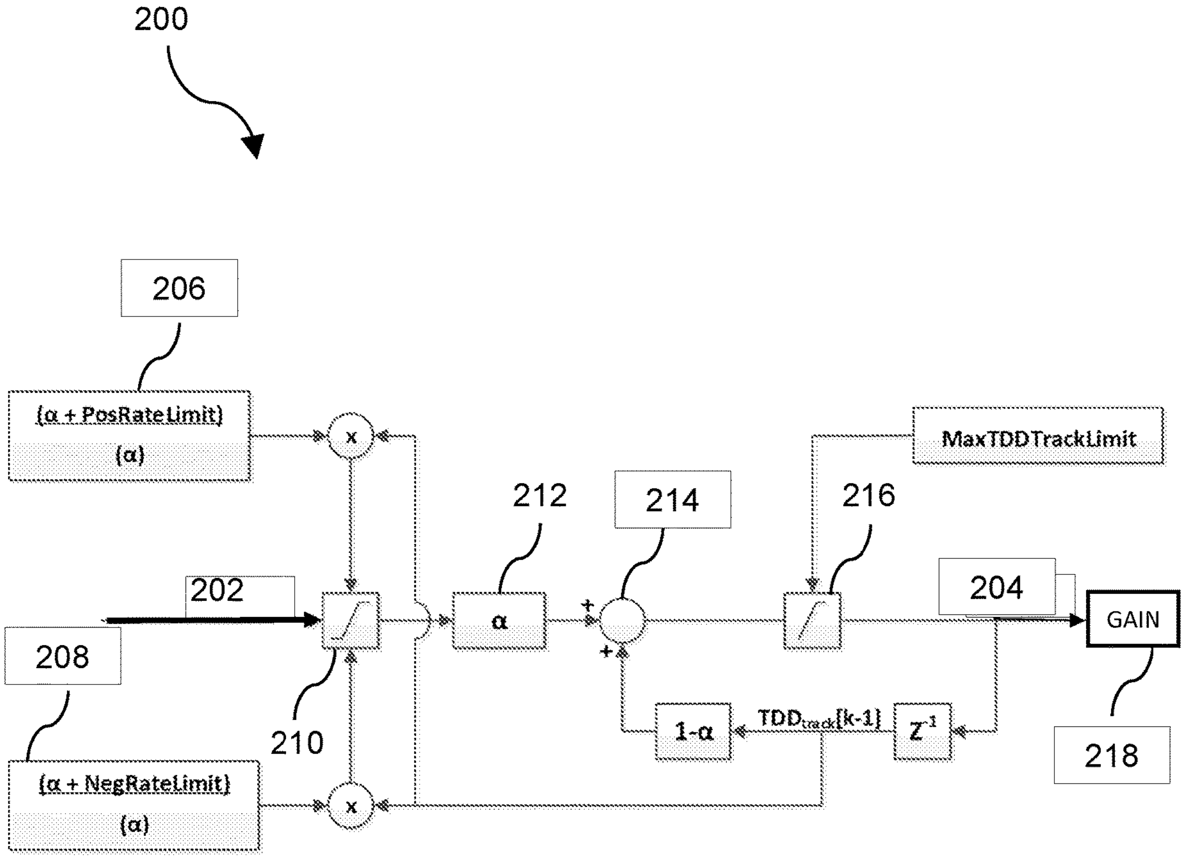
FIG. 3 shows a flowchart detailing various example logic, which may be applied when determining an amount of drug to be delivered in a meal bolus, in accordance with certain embodiments of the present disclosure.

FIG. 3 shows a filter 200 that can be used by the controller 28 to calculate filtered TDD values. The filter 200 receives one or more days of actual TDD calculations 202 and calculates a filtered TDD 204. The filter 200 can apply various limits such that actual TDD calculations that are outliers do not cause large variations in the calculated filtered TDD.

As one example, the filter 200 can initially place upper and lower limits on the rate of change of TDD. In FIG. 3, an upper limit component 206 and a lower limit component 208 can be programmed to place limits on the actual TDD calculations which effectively places limits on rate change limits to the actual TDD calculations. Both the upper limit component 206 and the lower limit component 208 are shown in FIG. 3 as including equations for programming the upper limit and the lower limit. Both the upper limit component 206 and the lower limit component 208 are shown as utilizing a programmable filter coefficient α. In certain embodiments, the programmable filter α coefficient is set between 0.1-0.5 with specific examples being 0.181 and 0.382. As will be described in more detail below, the programmable filter coefficient α can change based on the number of days (e.g., 3 days) since the controller 28 transitioned to the initial tracking phase.

The upper limit component 206 includes a term shown as "PosRateLimit" in FIG. 3. PosRateLimit is a positive rate limit ranging between 0.01-0.5 (e.g., 0.05, 0.3) that can change based on the number of days (e.g., 3 days) since transitioning to the initial tracking phase. The lower limit component 208 includes a term shown as "NegRateLimit" in FIG. 3. NegRateLimit is a negative rate limit ranging between −0.01 to −0.5 (e.g., −0.10, −0.3) that can change based on the number of days (e.g., 3 days) since transitioning to the initial tracking phase.

During the initial tracking phase, the terms of the upper limit component 206 and the lower limit component 208 can be set such that the TDD calculated at component 210 cannot exceed a 15% positive rate of change or 15% negative rate of change per day when the sampling period is 24 hours. As such, the component 210 can calculate a rate-limited TDD that may be a different value than the actual TDD 202 or, if the actual TDD 202 was within the rate limits, the same value as the actual TDD 202. The upper limit component 206 and the lower limit component 208 can be programmed to provide asymmetric or different absolute rate limits, which can be higher or lower than the 15% rate of change limit mentioned above.

At component 212 in FIG. 3, the rate-limited TDD is multiplied by the programmable filter coefficient α. At summing component 214, the output of component 212 is summed with the previously-calculated filtered TDD 204. Before calculating the filtered TDD 204, an overall maximum TDD limit is applied. TDD limit component 216 can be set to maximum limit on the filtered TDD 204. In certain embodiments, the TDD limit component 216 is dynamic such that the TDD limit component 216 can change over time. For example, the TDD limit component 216 could be based, at least in part, on a patient's insulin-to-carb ratio.

In certain embodiments, the maximum filtered TDD 204 is a function of TDB. For example, the maximum filtered TDD 204 can be limited to a scaling factor of the day's TDB (e.g., 1.5×, 2×, 3×, 4×). If the TDD calculation outputted by summing component 214 is greater than the maximum set by the TDD limit component 216, then the filtered TDD 204 will be set to equal the maximum TDD allowed by the TDD limit component 216.

Under the initial tracking phase, the controller 28 can apply the filter 200 such that the filtered TDD 204 takes into account multiple days (e.g., 3 days) of actual TDD 202 but with limits on the daily rate of change (e.g., ±15%) and the maximum permitted filtered TDD 204. The various components and limits (e.g., the programmable filter coefficient α, PosRateLimit, and NegRateLimit) of the filter 200 can be programmed and set such that the filtered TDD 204 takes into account multiple days of actual TDD 202 but that, at least partially, filters out events that are not indicative of a patient's insulin sensitivity. More specifically, the programmable filter coefficient α will establish how many days of actual TDD 202 calculations will be taken into account when calculating the filtered TDD 204 while the PosRateLimit and NegRateLimit will establish the rate limit at which the TDD changes day-to-day positively and negatively, respectively.

After operating according to the components and limits of the initial tracking phase for a certain period of time, the controller 28 can transition to a steady state tracking phase. For example, once the controller 28 has received a certain number of days (e.g., 4 days, 5 days) of actual TDD 202 calculations, the controller 28 can transition to a different phase that uses different values for the components and limits compared to those used during the initial tracking phase. The various values of the filter 200 can be chosen such that the transition from the initial tracking phase to a steady state tracking phase is smooth or abrupt.

During the steady state tracking phase, the controller 28 can program the filter 200 with different components and limits such that the filtered TDD 204 will likely vary less from day to day compared to the filtered TDD 204 during the initial tracking phase. For example, in some embodiments, the filter 200 can decrease the value of the programmable filter coefficient α to increase the number of days (e.g., from 3 days to 5 days) of actual TDD 202 calculations that are accounted for by the filter 200.

As another example, the value of the PosRateLimit component can be decreased to lower the positive rate limit for the actual TDD 202 calculations used by the filter 200. More specifically, in some embodiments, the PosRateLimit component can be set such that the upper limit component 206 limits the positive rate of change to 5% during the steady state tracking phase.

As another example, the value of the NegRateLimit component can be increased (e.g., to a less negative value) to lower the negative rate limit for the actual TDD 202 calculations used by the filter 200. More specifically, in some embodiments, the NegRateLimit component can be set such that the lower limit component 208 limits the negative rate of change to −10% during the steady state tracking phase. The lower limit component 208 can be set to permit a larger rate of change than the upper limit component 206 so that the controller 28 (via the MMPC 100) can decrease the filtered TDD 204 in the event a patient's insulin sensitivity rises quickly. If the MMPC 100 is delivering less insulin each day to a patient, the patient requires less insulin to maintain desired glucose levels and therefore is becoming more sensitive to insulin.

Whether in the initialization phase, the initial tracking phase, or the steady state tracking phase, the estimated TDD (in the case of the initialization phase) and the filtered TDD 204 (in the case of the tracking phases) can be used to set the gain 218 of the MMPC 100. Because the filtered TDD 204 may only be calculated once per day (under any of the phases), the gain 218 may also be adjusted once per day. In some embodiments, the gain 218 is adjusted multiple times a day.

The estimated TDD and the filtered TDD 204 can also be used to set an insulin sensitivity factor (ISF) of the above-described models.

As another example, the estimated TDD and the filtered TDD 204 can be used in the above-described objective function to set a weight coefficient for deviation of the control insulin trajectory above or below a predefined basal insulin profile which affects the amount of the correction micro-boluses. For example, when the estimated TDD and the filtered TDD 204 decreases over time, this indicates that the patient is more sensitive to insulin and therefore requires smaller insulin doses. As such, the insulin deviation terms of the objective function can greater penalize insulin deviations such that less insulin is delivered in the correction micro-boluses.

As another example, the estimated TDD and the filtered TDD 204 can be used set the threshold at which the MMPC 100 becomes less aggressive (e.g., when the MMPC 100 delivers less insulin for a given deviation). The threshold may be set in terms of units of IOB and breached when a patient's IOB crosses above the threshold.

As described above, the system 10 can, via the controller 28, calculate a first filtered TDD 204 during the initial tracking phase based, at least in part, on a first set of insulin delivery doses and subject to a first set of rate limits. The system 10 can also, via the controller 28, calculate a second filtered TDD 204 during the steady state tracking phase based, at least in part, on a second set of insulin delivery doses and subject to a second set of rate limits. In certain embodiments, the second set of insulin delivery doses includes at least some of the delivery doses from the first set of insulin delivery doses and an additional day or more of insulin delivery doses. As such, the first set of insulin delivery doses may be based on fewer actual TDD 202 calculations compared to the second set of insulin delivery doses. In certain embodiments, if no actual TDD 202 calculation is generated for a given day, the filtered TDD 204 may not be updated for that given day.

The first filtered TDD 204 can be used to set a first system gain 218 during the initial tracking phase, and the second filtered TDD 204 can be used to set a second system gain 218 during the steady state tracking phase. As such, the MMPC 100 will use the first system gain 218 to calculate some basal doses and the second system gain 218 to calculate other basal doses.

In the process of calculating the first filtered TDD 204, the filter 200 applies a first set of rate limits, which include a first upper limit and a first lower limit. In the process of calculating the second filtered TDD 204, the filter 200 applies a second set of rate limits, which include a second upper limit and a second lower limit. As described above, the first set of rate limits permit greater TDD rate changes than the second set of rate limits. And, in certain embodiments, the second lower limit permits a greater rate change than the second upper limit. The filter 200 can also limit the filtered TDD 204 to a maximum value, which can be based on a predetermined ratio of TDB.

In certain embodiments, the filter 200 is a digital filter such as an infinite impulse response (IIR) filter that processes actual TDD 202 to calculate the filtered TDD 204. Further, the upper limit component 206 and the lower limit component 208 can considered to "clip" the input (e.g., the actual TDD 202) to the filter 200.

As noted above, the controller 28 can include at least one processor 34 that executes control logic stored in the memory 36, which is included with or coupled to the controller 28. The memory 36 can store the control logic in the form of executable instructions 38 (e.g., computer code, machine-useable instructions, and the like) for causing the processor 34 to implement the various functions and methods described herein.

Methods

Figure 4:
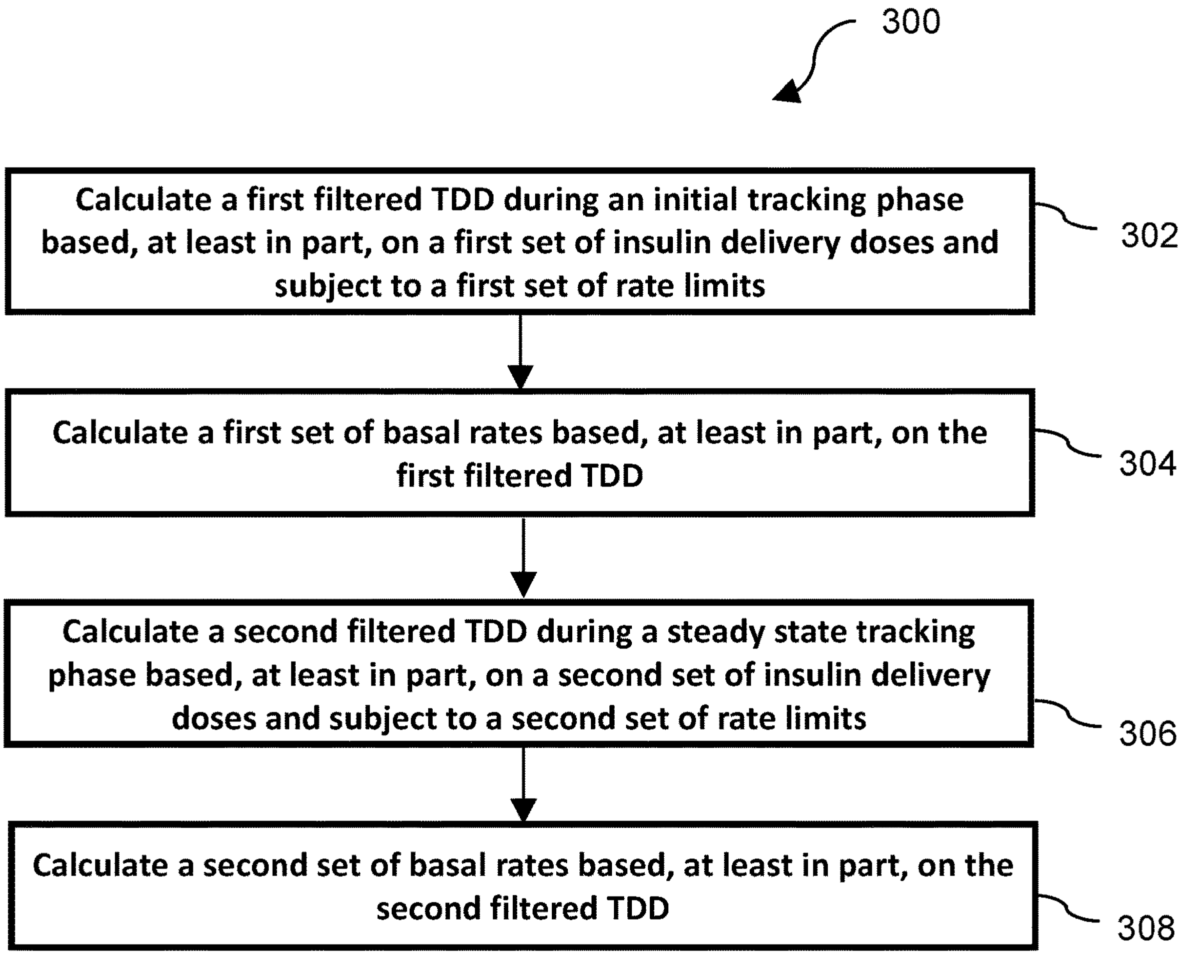
FIG. 4 shows a block diagram of a method, in accordance with certain embodiments of the present disclosure.

FIG. 4 shows a flowchart of a method 300 that can be carried out with the system 10 to calculate filtered TDD 204, which can be used in replace of or as a proxy for a patient's insulin sensitivity. The method 300 includes calculating, by the controller 28 applying a digital filter 200, a first filtered TDD 204 during an initial tracking phase based, at least in part, on a first set of insulin delivery doses and subject to a first set of rate limits (block 302 in FIG. 4). The method 300 also includes calculating, by the controller, a first set of basal rates based, at least in part, on the first filtered TDD 204 (block 304 in FIG. 4). The method 300 further includes calculating, by the controller 28 applying the digital filter 200, a second filtered TDD 204 during a steady state tracking phase based, at least in part, on a second set of insulin delivery doses and subject to a second set of rate limits (block 306 in FIG. 4). The method 300 further includes calculating, by the controller, a second set of basal rates based, at least in part, on the second filtered TDD 204 (block 308 in FIG. 4).

CONCLUSION

Various alternatives and modifications may be devised by those skilled in the art without departing from the present disclosure. In particular, although the disclosure uses a model-based controller to ultimately determine and deliver an appropriate amount of insulin to a patient, features of the disclosure can apply to other types of control algorithms (e.g., PID control algorithm, a fuzzy logic control algorithm, and the like).

Accordingly, the present disclosure is intended to embrace all such alternatives, modifications and variances. Additionally, while several embodiments of the present disclosure have been illustrated in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A system to control glucose in a patient, the system comprising:
- a controller configured to communicate with a medication delivery device and including control logic operative to:
  - calculate a first filtered total daily dose (TDD) during an initial tracking phase based, at least in part, on a first set of insulin delivery doses and subject to a first set of rate limits, and
  - calculate a second filtered TDD during a steady state tracking phase based, at least in part, on a second set of insulin delivery doses and subject to a second set of rate limits, wherein the first set of insulin delivery doses differs from the second set of insulin delivery doses and the first set of rate limits differs from the second set of rate limits, and
  - wherein the control logic is operative to transition to the steady state tracking phase after applying the initial tracking phase for a period of time or in response to a pre-determined number of valid actual TDD measurements.

2. The system of claim 1, wherein the control logic is further operative to:
- set a first system gain based, at least in part, on the first filtered TDD, and
- set of second system gain based, at least in part on the second filtered TDD.

3. The system of claim 2, wherein the control logic is further operative to:
- calculate a first set of basal doses based, at least in part, on the first system gain, and
- calculate a second set of basal doses based, at least in part on the second system gain.

4. The system of claim 1, wherein the first set of rate limits includes a first upper limit and a first lower limit, wherein the second set of rate limits includes a second upper limit and a second lower limit, wherein the first set of rate limits permit greater TDD rate changes than the second set of rate limits.

5. The system of claim 4, wherein the second lower limit permits a greater absolute rate change than the second upper limit.

6. The system of claim 1, wherein the first set of insulin delivery doses are based on fewer TDD measurements than the second set of insulin delivery doses.

7. The system of claim 1, wherein the control logic is further operative to:
- calculate an estimated TDD at start-up of an initialization phase based, at least in part, on a total daily basal (TDB) level.

8. The system of claim 7, wherein the estimated TDD is a pre-determined ratio of TDB.

9. The system of claim 1, wherein the first filtered TDD and the second filtered TDD are limited to a pre-determined ratio of total daily basal.

10. The system of claim 1, wherein the control logic is operative to:
- calculate the first filtered TDD during the initial tracking phase once per day, and
- calculate the second filtered TDD during the steady state tracking phase once per day.

11. The system of claim 1, wherein the control logic is operative to:
- calculate the first filtered TDD by processing the first set of insulin delivery doses with an infinite impulse response (IIR) filter, and
- calculate the second filtered TDD by processing the second set of insulin delivery doses with the IIR filter.

12. The system of claim 1, further comprising:
- the medication delivery device configured to deliver insulin to the patient based, at least in part, to the first filtered TDD during the initiation tracking phase and the second filtered TDD during the steady state tracking phase.

13. The system of claim 12, further comprising the insulin contained in the medication delivery device.

14. The system of claim 1, further comprising:
- a glucose measurement device in communication with the controller and configured to measure the glucose level.

15. A method comprising:
- calculating, by a controller applying a digital filter, a first filtered total daily dose (TDD) during an initial tracking phase based, at least in part, on a first set of insulin delivery doses and subject to a first set of rate limits;
- calculating, by the controller, a first set of basal rates based, at least in part, on the first filtered TDD;
- calculating, by the controller applying the digital filter, a second filtered TDD during a steady state tracking phase based, at least in part, on a second set of insulin delivery doses and subject to a second set of rate limits, wherein the first set of insulin delivery doses differs from the second set of insulin delivery doses and the first set of rate limits differs from the second set of rate limits; and
- calculating, by the controller, a second set of basal rates based, at least in part, on the second filtered TDD,
- wherein the controller is operative to transition to the steady state tracking phase after applying the initial tracking phase for a period of time or in response to a pre-determined number of valid actual TDD measurements.

16. The method of claim 15, further comprising:
- delivering, by a medication delivery device, amounts of insulin responsive to the first set of basal rates; and
- delivering, by the medication delivery device, amounts of insulin responsive to the second set of basal rates.

17. The method of claim 15, further comprising:
- setting a first system gain based, at least in part, on the first filtered TDD, and
- setting of second system gain based, at least in part on the second filtered TDD, wherein the first set of basal rates based, at least in part, on the first system gain, wherein the second set of basal rates based, at least in part, on the second system gain.

18. The method of claim 15, further comprising:
- calculating an estimated TDD during an initialization phase based, at least in part, on a total daily basal level.

19. The method of claim 15, wherein the first filtered TDD and the second filtered TDD are limited to a pre-determined ratio of a total daily basal level.

20. A non-transitory computer-readable medium including instructions that, when executed, cause a hardware processor to:
- calculate a first filtered total daily dose (TDD) during an initial tracking phase based, at least in part, on a first set of insulin delivery doses and subject to a first set of rate limits; and calculate a second filtered TDD during a steady state tracking phase based, at least in part, on a second set of insulin delivery doses and subject to a second set of rate limits, wherein the first set of insulin delivery doses differs from the second set of insulin delivery doses and the first set of rate limits differs from the second set of rate limits, and wherein the processor is operative to transition to the steady state tracking phase after applying the initial tracking phase for a period of time or in response to a pre-determined number of valid actual TDD measurements.

* * * * *